(12) United States Patent
Hwang et al.

(10) Patent No.: US 10,456,775 B2
(45) Date of Patent: Oct. 29, 2019

(54) METHOD OF PREPARING ZINC FERRITE CATALYST

(71) Applicant: LG CHEM, LTD., Seoul (KR)

(72) Inventors: Ye Seul Hwang, Daejeon (KR); Dong Hyun Ko, Daejeon (KR); Kyong Yong Cha, Daejeon (KR); Dae Heung Choi, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 15/750,806

(22) PCT Filed: Mar. 16, 2017

(86) PCT No.: PCT/KR2017/002835
§ 371 (c)(1),
(2) Date: Feb. 6, 2018

(87) PCT Pub. No.: WO2017/171278
PCT Pub. Date: Oct. 5, 2017

(65) Prior Publication Data
US 2018/0229221 A1    Aug. 16, 2018

(30) Foreign Application Priority Data
Mar. 28, 2016 (KR) .................. 10-2016-0037007

(51) Int. Cl.
*B01J 23/00* (2006.01)
*B01J 23/80* (2006.01)
*B01J 37/03* (2006.01)
*B01J 37/04* (2006.01)
*B01J 37/08* (2006.01)
*C01G 49/00* (2006.01)

(52) U.S. Cl.
CPC ............ *B01J 23/80* (2013.01); *B01J 37/031* (2013.01); *B01J 37/04* (2013.01); *B01J 37/08* (2013.01); *C01G 49/0063* (2013.01); *C01P 2002/72* (2013.01)

(58) Field of Classification Search
CPC ..... C01G 49/0063; B01J 23/06; B01J 23/745; B01J 23/80; B01J 37/031; B01J 37/08
USPC .................. 423/140–147, 594.1; 502/329
See application file for complete search history.

(56) References Cited

U.S. PATENT DOCUMENTS

| | | | | |
|---|---|---|---|---|
| 3,303,235 A * | 2/1967 | Croce | .................. | C07C 5/48 585/618 |
| 3,378,335 A * | 4/1968 | Ellis | .................. | C01B 13/14 252/62.56 |
| 3,645,672 A * | 2/1972 | Cowlard et al. | ..... | C01G 49/009 252/62.56 |
| 3,951,869 A * | 4/1976 | Baker | .................. | B01J 23/8892 502/324 |
| 4,664,831 A * | 5/1987 | Hibst | .................. | B82Y 30/00 252/62.56 |
| 6,193,904 B1 * | 2/2001 | Schoch, Jr. | .......... | C01G 49/009 252/62.56 |

FOREIGN PATENT DOCUMENTS

| | | |
|---|---|---|
| CN | 1169745 | * 10/2004 |
| CN | 102974357 | 3/2013 |
| DE | 2252573 | * 6/1973 |
| GB | 739069 | * 10/1955 |
| JP | S51131807 | 11/1976 |
| JP | H03115106 | 5/1991 |
| JP | H08208323 | 8/1996 |
| JP | 2002371074 | 12/2002 |
| JP | 2015167886 | 9/2015 |
| KR | 10-0847206 | 7/2008 |
| KR | 10-0950373 | 3/2010 |
| KR | 10-0961394 | 6/2010 |
| KR | 10-1340621 | 12/2013 |
| KR | 10-1472230 | 12/2014 |
| WO | 2009/045002 | * 4/2009 |

OTHER PUBLICATIONS

Translation of DE-2252573A1, Jun. 14, 1973. (Year: 1973).*
Translation of CN 1169745, Oct. 6, 2004. (Year: 2004).*
Translation of Japan 2015-167886. (Year: 2015).*
Berbenni et al., "Synthesis and magnetic properties of ZnFe2O4 obtained by mechanochemically assisted low-temperature annealing of mixtures of Zn and Fe oxalates," Thermochimica Acta 447: 184-189 (2006).

(Continued)

*Primary Examiner* — Steven J Bos
(74) *Attorney, Agent, or Firm* — Dentons US LLP

(57) ABSTRACT

The present disclosure relates to a method of preparing a zinc ferrite catalyst. More particularly, the present invention relates to a method of preparing a zinc ferrite catalyst comprising a) a step of dissolving a zinc precursor and an iron (III) precursor in water to prepare an aqueous metal precursor solution; b) a step of precipitating a solid catalyst precursor while vaporizing water in the aqueous metal precursor solution; and c) a step of firing the precipitated solid catalyst precursor to prepare a zinc ferrite catalyst. In accordance with the present disclosure, the method of preparing a zinc ferrite catalyst can be simply carried out without a pH adjustment step and can secure reproducibility.

7 Claims, 2 Drawing Sheets

(56) References Cited

OTHER PUBLICATIONS

Kumar et al., "Simple synthesis and magnetic properties of nickel-zinc ferrites nanoparticles by using Aloe vera extract solution," Archives of Applied Science Research 5(6): 145-151 (2013).

Langbein, H. and S. Fischer, "Investigation of the formation of nickel-zinc ferrite from coprecipitated oxalates," Thermochimica Acta 182(1): 39-46 (1991).

Diodati et al., "Coprecipitation of Oxalates: An Easy and Reproducible Wet-Chemistry Synthesis Route for Transition-Metal Ferrites," European Journal of Inorganic Chemistry 2014(5): 875-887 (2013).

* cited by examiner

[FIG. 1]
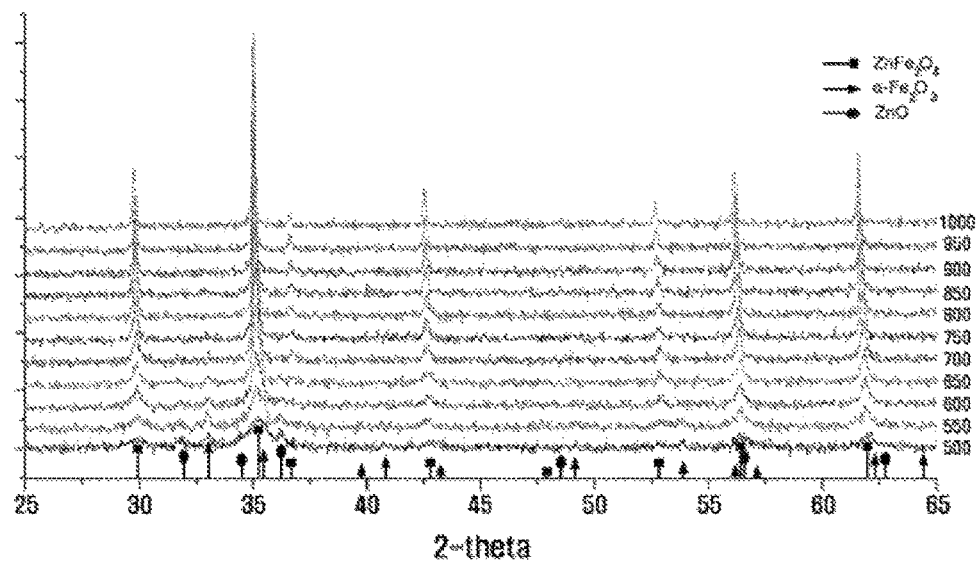
[FIG. 2]
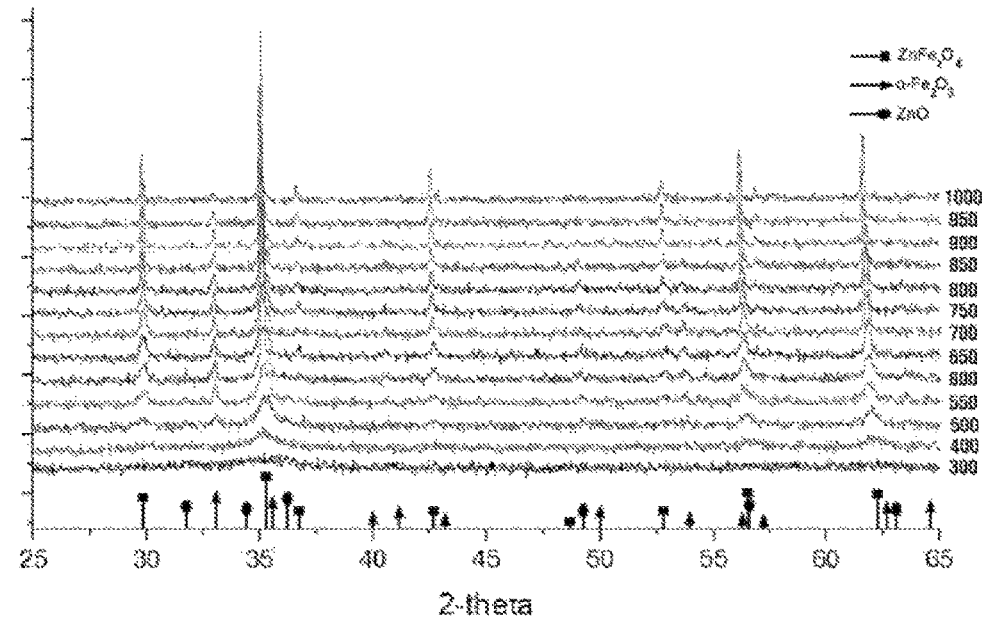

[FIG. 3]
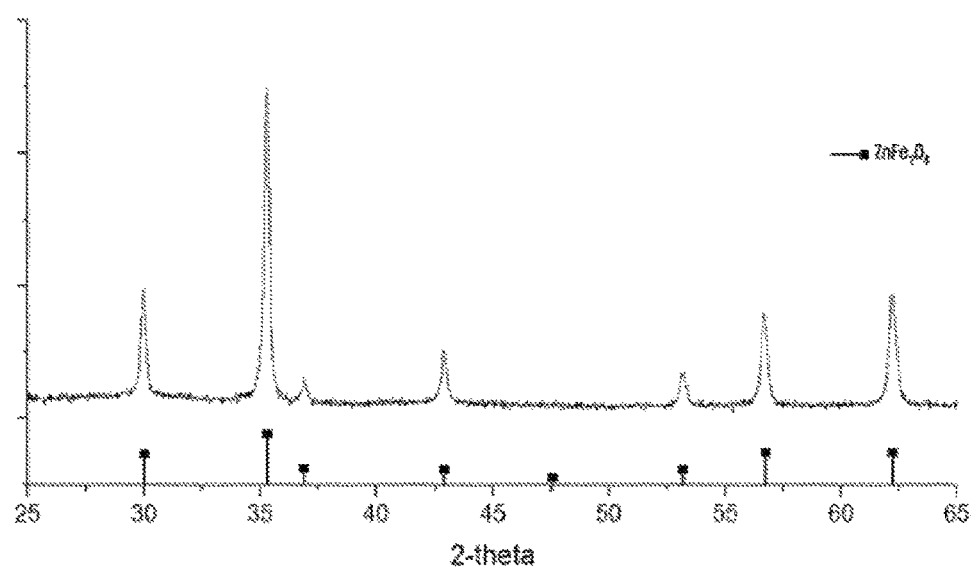

METHOD OF PREPARING ZINC FERRITE CATALYST

CROSS-REFERENCE TO RELATED APPLICATION

This application is a National Stage Application of International Application No. PCT/KR2017/002835 filed on Mar. 16, 2017, which claims priority to and the benefit of Korean Patent Application No. 10-2016-0037007, filed on Mar. 28, 2016 in the Korean Intellectual Property Office, both of which are incorporated herein in their entirety by reference for all purposes as if fully set forth herein.

TECHNICAL FIELD

The present disclosure relates to a method of preparing a zinc ferrite catalyst. More particularly, the present invention relates to a method of preparing a zinc ferrite catalyst which is capable of providing a simplified preparation process due to omission of a pH adjustment step, stable synthesis without change in an iron oxidation state, and excellent reproducibility.

BACKGROUND ART 1,3-Butadiene is used as an intermediate in producing petrochemical products and demand therefor and value thereof are gradually increasing throughout the world. Such 1,3-butadiene is produced by naphtha cracking, direct dehydrogenation of butene, oxidative dehydrogenation of butene, or the like. However, since a naphtha cracking process has high energy consumption due to high reaction temperature and a problem that other basic oils other than 1,3-butadiene are produced in a surplus because the process is not highly selective for 1,3-butadiene. In addition, direct dehydrogenation of n-butene is not only thermodynamically disadvantageous, but also requires high-temperature and low-pressure conditions for the production of 1,3-butadiene with high yield due to being an endothermic reaction. Accordingly, direct dehydrogenation of n-butene is not suitable for industrial production of 1,3-butadiene.

Meanwhile, oxidative dehydrogenation of butene is a reaction in which butene and oxygen react with each other in the presence of a metal oxide catalyst to produce 1,3-butadiene and water. Since stable water is produced by the reaction, the reaction is thermodynamically advantageous. In addition, oxidative dehydrogenation of butene is exothermic, unlike direct dehydrogenation of butene, 1,3-butadiene may be obtained in a high yield even at a low reaction temperature as compared to direct dehydrogenation. Further, since oxidative dehydrogenation of butene does not require additional heat supply, it may become an effective stand-alone production process to meet demand for 1,3-butadiene.

The metal oxide catalyst is generally synthesized by a precipitation method and, in the precipitation method, the pHs of an aqueous metal oxide precursor solution, an aqueous basic solution, and a coprecipitation solution and the like are important synthesis variables. Accordingly, the precipitation method has problems such as a complex preparation process and poor reproducibility.

Therefore, there is a need for a simple catalyst preparation method capable of securing reproducibility.

RELATED ART DOCUMENT (Patent Document 1) KR Patent No. 10-0961394 B1

DISCLOSURE

Technical Problem

Therefore, the present invention has been made in view of the above problems, and it is one object of the present invention to provide a method of preparing a zinc ferrite catalyst which is capable of providing a simplified preparation process due to omission of a pH adjustment step, stable synthesis without change in an iron oxidation state, and sufficiently secured reproducibility.

The above and other objects can be accomplished by the present disclosure described below.

Technical Solution

In accordance with one aspect of the present invention, provided is a method of preparing a zinc ferrite catalyst, the method including a) a step of dissolving a zinc precursor and an iron (III) precursor in water to prepare an aqueous metal precursor solution; b) a step of precipitating a solid catalyst precursor while vaporizing water in the aqueous metal precursor solution; and c) a step of firing the precipitated solid catalyst precursor to prepare a zinc ferrite catalyst.

Advantageous Effects

As apparent from the fore-going, the present disclosure provides a method of preparing a zinc ferrite catalyst which is capable of providing stable synthesis without change in an iron oxidation state, a simplified preparation process due to omission of a pH adjustment, and sufficiently secured reproducibility.

DESCRIPTION OF DRAWINGS

FIG. 1 illustrates a stacked X-ray diffraction (XRD) data result of catalysts prepared in Examples 1 to 11 according to the present invention.

FIG. 2 illustrates a stacked XRD data result of catalysts prepared in Examples 12 to 22 and Comparative Examples 2 and 3 according to the present invention.

FIG. 3 illustrates XRD data of a catalyst prepared in Comparative Example 1 not according to the present invention.

BEST MODE

Hereinafter, the present invention is described in detail.

A method of preparing a zinc ferrite catalyst of the present disclosure includes a) a step of dissolving a zinc precursor and an iron (III) precursor in water to prepare an aqueous metal precursor solution; b) a step of precipitating a solid catalyst precursor while vaporizing water in the aqueous metal precursor solution; and c) a step of firing the precipitated solid catalyst precursor to prepare a zinc ferrite catalyst. In this case, a zinc ferrite catalyst may be prepared without a pH adjustment step, whereby a preparation process thereof is simple and reproducibility is secured.

A mole ratio of the zinc precursor to the iron (III) precursor may be, for example, 5:1 to 1:1, 2:1 to 1:1, or 1:1 to 1:5. Within this range, a zinc ferrite ($ZnFe_2O_4$) phase is predominantly formed, whereby selectivity and yield according to oxidative dehydrogenation are superior.

The aqueous metal precursor solution may include, for example, 0.1 to 30% by weight or 0.1 to 10% by weight of the metal precursors. Within this range, the metal precursor is completely dissolved in a solvent.

The zinc precursor may be, for example, zinc oxalate. In this case, the zinc ferrite catalyst is superiorly formed.

The iron (III) precursor may be, for example, iron (III) oxalate. In this case, the zinc ferrite catalyst is superiorly formed.

The vaporization may be carried out, for example, until 80 to 99% by weight or 90 to 99% by weight of water is removed based on a total weight of added water. Within this range, a solid zinc ferrite catalyst may be precipitated while vaporizing water without an additional filtration step and drying step.

The vaporization may be carried out, for example, at 60 to 80° C. or 65 to 75° C. for 2 to 4 hours or 2.5 to 3.5 hours by means of an evaporator. Within this range, a solid zinc ferrite catalyst is effectively precipitated.

The firing may be carried out, for example, at 500 to 1200° C., 600 to 1100° C., or 700 to 1000° C. Within this range, a zinc ferrite ($ZnFe_2O_4$) phase is predominantly formed, and thus, selectivity and yield according to oxidative dehydrogenation are superior.

The firing may be carried out, for example, for 1 to 12 hours, 2 to 8 hours, or 2 to 5 hours. Within this range, a zinc ferrite ($ZnFe_2O_4$) phase is predominantly formed, and thus, selectivity and yield according to oxidative dehydrogenation are superior.

The zinc ferrite may be, for example, a single-phase $ZnFe_2O_4$. In this case, selectivity and yield according to oxidative dehydrogenation are superior.

With regard to step b), for example, a process of preparing an aqueous metal precursor solution by mixing zinc oxalate and iron (III) oxalate in a mole ratio of 1:1 and precipitating a solid zinc/iron oxalate while vaporizing water is represented by Formula 1 below:

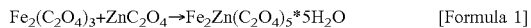

$$Fe_2(C_2O_4)_3 + ZnC_2O_4 \rightarrow Fe_2Zn(C_2O_4)_5 \cdot 5H_2O \quad \text{[Formula 1]}$$

With regard to step c), for example, a process of firing a precipitated solid zinc/iron oxalate at 1000° C. for 3 hours to form zinc ferrite is represented by Formula 2 below. In the firing process, CO and $CO_2$ are removed.

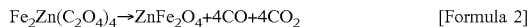

$$Fe_2Zn(C_2O_4)_4 \rightarrow ZnFe_2O_4 + 4CO + 4CO_2 \quad \text{[Formula 2]}$$

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Examples 1 to 11

3.2 g of zinc oxalate and 8.2 g of iron (III) oxalate (in a mole ratio of 1:1) were dissolved in 800 ml of distilled water, thereby preparing 810 g of an aqueous metal precursor solution. Catalyst precursors were precipitated while vaporizing water from the aqueous metal precursor solution at 70° C. over a period of 3 hours by means of an evaporator until 99% by weight of a total amount of added water was removed.

The precipitated catalyst precursors were respectively fired at 500, 550, 600, 650, 700, 750, 800, 850, 900, 950 and 1000° C. for 3 hours in an air atmosphere, thereby preparing zinc ferrite catalysts. Each of the prepared zinc ferrite catalysts was subjected to XRD measurement. As a result, a $ZnFe_2O_4$ phase was predominantly formed. Particularly, a single-phase $ZnFe_2O_4$ was formed at firing temperatures of 700, 750, 800, 850, 900, 950, and 1000° C. Accordingly, it was confirmed that the zinc ferrite catalysts were reproducibly synthesized. XRD data for each firing temperature was stacked. A result is illustrated in FIG. 1.

Examples 12 to 22

2.4 g of zinc oxalate and 9.4 g of iron (III) oxalate (in a mole ratio of 1:1.5) were dissolved in 800 ml of distilled water, thereby preparing 810 g of an aqueous metal precursor solution. Catalyst precursors were precipitated while vaporizing water from the aqueous metal precursor solution at 70° C. over a period of 3 hours by means of an evaporator until 99% by weight of a total amount of added water was removed.

The precipitated catalyst precursors were respectively fired at 500, 550, 600, 650, 700, 750, 800, 850, 900, 950 and 1000° C. for 3 hours in an air atmosphere, thereby preparing zinc ferrite catalysts. Each of the prepared zinc ferrite catalysts was subjected to XRD measurement. As a result, a $ZnFe_2O_4$ phase was predominantly formed. Accordingly, it was confirmed that the zinc ferrite catalysts were reproducibly synthesized. XRD data for each firing temperature was stacked. A result is illustrated in FIG. 1.

Comparative Example 1

1.0 g of zinc chloride and 4.1 g of iron (III) chloride (in a mole ratio of 1:2) were dissolved in 700 ml of distilled water, thereby preparing 710 g of an aqueous metal precursor solution. 18 g of an aqueous 3 M NaOH solution was added dropwise to the aqueous metal precursor solution to adjust pH of a final solution to 9. A generated slurry-type solution was filtered, washed with 1000 ml of distilled water, and dried at 90° C. The dried cake-type catalyst precursor was fired at 700° C. for 3 hours, thereby preparing a zinc ferrite catalyst. The prepared zinc ferrite catalyst was subjected to XRD measurement. As a result, formation of a $ZnFe_2O_4$ phase was confirmed. This result is illustrated in FIG. 3.

Comparative Examples 2 and 3

Zinc ferrite catalysts were prepared in the same manner as in Example 2, except that precipitated catalyst precursors were respectively fired at 300 and 400° C. for 3 hours in an air atmosphere. The prepared zinc ferrite catalysts were subjected to XRD measurement. As a result, it was confirmed that a catalyst was not generated. This result is illustrated in FIG. 2.

The invention claimed is:
1. A method of preparing a zinc ferrite catalyst, the method comprising:
   a) dissolving a zinc precursor and an iron (III) precursor in water to prepare an aqueous metal precursor solution;
   b) precipitating a solid catalyst precursor by vaporizing the water in the aqueous metal precursor solution, wherein the vaporizing is carried out at 60 to 80° C. for 2 to 4 hours using an evaporator; and c) firing the precipitated solid catalyst precursor at a temperature from 850° C. to 1000° C. to prepare the zinc ferrite catalyst.

2. The method according to claim 1, wherein a mole ratio of the zinc precursor to the iron (III) precursor is 5:1 to 1:1.

3. The method according to claim 1, wherein the aqueous metal precursor solution comprises 0.1 to 10% by weight of the metal precursors.

4. The method according to claim 1, wherein the zinc precursor is zinc oxalate.

5. The method according to claim 1, wherein the iron (III) precursor is iron (III) oxalate.

6. The method according to claim 1, wherein the vaporizing is carried out until 80 to 99% by weight of a total amount of water in the aqueous metal precursor solution is removed.

7. The method according to claim 1, wherein the firing is carried out for 1 to 12 hours.

\* \* \* \* \*